(12) United States Patent
Li et al.

(10) Patent No.: US 12,188,867 B1
(45) Date of Patent: Jan. 7, 2025

(54) METHOD FOR INVERSING DEPTH OF SUBSURFACE CHLOROPHYLL-A MAXIMA OF OCEANIC WATER BODY BASED ON REMOTE SENSING REFLECTANCE

(71) Applicant: Guangdong Ocean University, Zhanjiang (CN)

(72) Inventors: Junyi Li, Zhanjiang (CN); Lingling Xie, Zhanjiang (CN); Min Li, Zhanjiang (CN); Xiaomin Ye, Beijing (CN); Tao He, Zhanjiang (CN)

(73) Assignee: Guangdong Ocean University, Zhanjiang (CN)

( * ) Notice: Subject to any disclaimer, the term of this patent is extended or adjusted under 35 U.S.C. 154(b) by 0 days.

(21) Appl. No.: 18/890,715

(22) Filed: Sep. 19, 2024

Related U.S. Application Data

(63) Continuation of application No. PCT/CN2024/106640, filed on Jul. 22, 2024.

(30) Foreign Application Priority Data

Dec. 19, 2023 (CN) .......................... 202311760855.X

(51) Int. Cl.
*G01N 21/55* (2014.01)
*G01N 21/31* (2006.01)
*G01N 33/18* (2006.01)

(52) U.S. Cl.
CPC .............. *G01N 21/55* (2013.01); *G01N 21/31* (2013.01); *G01N 33/18* (2013.01); *G01N 2021/557* (2013.01); *G01N 2201/126* (2013.01)

(58) Field of Classification Search
CPC ........ G01N 21/55; G01N 21/31; G01N 33/18; G01N 2021/557; G01N 2207/126
See application file for complete search history.

(56) References Cited

PUBLICATIONS

Bouman et al. (Vertical structure in chlorophyll profiles: influence on primary production in the Arctic Ocean. Philos Trans A Math Phys Eng Sci. Oct. 2, 2020;378(2181):20190351. doi: 10.1098/rsta.2019.0351. Epub Aug. 31, 2020. PMID: 32862808; PMCID: PMC7481674.) (Year: 2020).*

Gittings et al. (Evaluating tropical phytoplankton phenology metrics using contemporary tools. Sci Rep. Jan. 24, 2019;9(1):674. doi: 10.1038/s41598-018-37370-4. PMID: 30679755; PMCID: PMC6345824.) (Year: 2019).*

* cited by examiner

*Primary Examiner* — Lisa M Caputo
*Assistant Examiner* — Christian T Bryant

(57) ABSTRACT

A method for inversing a depth of a subsurface chlorophyll-a maxima (SCM) of an oceanic water body based on remote sensing reflectance is provided. The method includes: band selection, R value calculation, data collection, model construction, and $Z_{SCM}$ calculation. This method can not only reduce the dependence of machine learning on sea surface chlorophyll-a concentrations, sea surface temperature data and sea surface height data, and reduce the calculation resource consumption of running machine learning, but also effectively improve the inversion accuracy, and effectively reduce the calculation resource consumption and inversion difficulty of inversing the SCM.

8 Claims, 2 Drawing Sheets

METHOD FOR INVERSING DEPTH OF SUBSURFACE CHLOROPHYLL-A MAXIMA OF OCEANIC WATER BODY BASED ON REMOTE SENSING REFLECTANCE

CROSS-REFERENCE TO RELATED APPLICATION

This application claims priority to Chinese Patent Application No. 202311760855.X, filed on Dec. 19, 2023, which is herein incorporated by reference in its entirety.

TECHNICAL FIELD

The disclosure relates to the field of preparation of water color remote sensing technologies, particularly to a method for inversing a depth of a subsurface chlorophyll-a maxima of an oceanic water body based on remote sensing reflectance.

BACKGROUND

Phytoplankton is an important part of an ocean and plays an important role in a marine ecosystem, and contributes about 50% of a global primary productivity. Chlorophyll-a (also referred to as chl-a) is a main pigment in cells of the marine phytoplankton, and it is an important indicator to measure the amount of the marine phytoplankton. As a producer in the marine ecosystem, the marine phytoplankton provides basic materials and energy for the whole marine ecosystem through photosynthesis. Furthermore, the marine phytoplankton is a natural bait for marine organisms such as shellfish, shrimp and fish larvae, and these marine organisms will migrate with the change of the chlorophyll-a concentration. Therefore, a vertical distribution of the chlorophyll-a concentration in the ocean is uneven, however, the chlorophyll-a concentration obtained by traditional remote sensing is often an integral of a concentration of a chlorophyll-a in a whole water column, so observing a vertical structure of the chlorophyll-a concentration has become an urgent problem to be solved in the water color remote sensing technologies. Studies show that there is always a maximum chlorophyll-a concentration in an ocean subsurface, which is called a subsurface chlorophyll-a maxima (SCM). A depth of an SCM of an oceanic water body is an important index to estimate a vertical distribution of the chlorophyll-a, a key parameter to estimate a global carbon flux and the global primary productivity, an important index to measure an ecological effect caused by global climate change, and one of key parameters to be solved urgently in ocean color remote sensing. A remote sensing reflectance signal in an ocean region is mainly influenced by the vertical distribution and chlorophyll-a concentration, and remote sensing reflectance characteristics generated by distribution of the remote sensing reflectance signal can effectively indicate the depth of the SCM. Inversing and obtaining the depth of the SCM based on the remote sensing reflectance is an important basis for understanding a primary productivity of the ocean, and it is of great significance to water ecological protection, global carbon cycle and global climate change on a macro scale.

At present, the inversing of the SCM of the oceanic water body mainly includes a method for inversing the depth of the SCM based on a Gaussian kernel function model and a method for inversing the depth of the SCM based on machine learning. The details for the above two methods are as follows. (1) For the method for inversing the depth of the SCM based on the Gaussian kernel function model: firstly, it is assumed that the vertical distribution of the chlorophyll-a concentration to a Gaussian function:

$$Chla(z) = Chla_0 + \frac{h}{\sigma\sqrt{2\pi}}\exp\left[-\frac{(Z-Z_{scm})^2}{2\sigma^2}\right].$$

$Z_{scm}$ represents the depth of the SCM, which indicates the depth where the SCM is located, and this method can estimate the depth of the SCM by using a chlorophyll-a concentration in a sea surface inversed by satellite. However, this method is very dependent on an inversion accuracy of the subsurface chlorophyll-a concentration, and the subsurface chlorophyll-a concentration does not all conform to Gaussian function distribution, so the inversion accuracy of this method is lower, and the calculation method is complicated and requires a large amount of calculation. (2) For the method for inversing the depth of the SCM based on the machine learning: at present, the method needs many parameters, such as sea surface temperature, sea surface height and sea surface chlorophyll-a concentration. Moreover, this method needs a lot of chlorophyll-a profile data for training. In the process of machine learning model training, a lot of computing resources need to be consumed, which is expensive. Therefore, it is particularly important to propose an algorithm for calculating the depth of the SCM only by remote sensing reflectance.

In addition, the method for inversing the depth of the SCM based on the Gaussian kernel function model and the method for inversing the depth of the SCM based on the machine learning still have the shortcomings of lack of effective optical and physical basis, and can not make good use of the remote sensing reflectance characteristics caused by the depth of the SCM.

SUMMARY

(1) Technical Problems to be Solved

Aiming at the shortcomings of the related art, the disclosure provides a method for inversing a depth of an SCM of an oceanic water body based on remote sensing reflectance. It could solve the problem that the method for inversing the depth of the SCM based on the Gaussian kernel function model and the method for inversing the depth of the SCM based on the machine learning still have the shortcomings of lack of effective optical and physical basis.

(2) Technical Solutions

In order to achieve the above objectives, the following technical solutions are provided.

In an embodiment, a method for inversing a depth of an SCM of an oceanic water body based on remote sensing reflectance is provided, which includes: step 1, band selection, including: obtaining a remote sensing reflectance data from a moderate-resolution imaging spectroradiometer (MODIS) remote sensing data, and selecting target remote sensing reflectance data corresponding to three bands of 412 nanometers (nm), 555 nm and 678 nm from the remote sensing reflectance data; step 2, R value calculation, including: calculating a difference between a remote sensing reflectance corresponding to the band 412 nm from the target remote sensing reflectance data and a remote sensing reflectance corresponding to the band 678 nm from the target remote sensing reflectance data, and calculating a ratio of the difference to a remote sensing reflectance corresponding to the band 555 nm from the target remote sensing reflectance data as a R value; step 3, data collection, including: obtaining groups of global measured biogeochemical-automatic reporting oceanographic observers (BGC-Argo) chlorophyll-a concentration profile data, fitting a BGC-Argo chlorophyll-a profile by using a Gaussian function according to the groups of global measured BGC-Argo chlorophyll-a concentration profile data, calculating a depth of an SCM of each group of the groups of global measured BGC-Argo chlorophyll-a concentration profile data according to the BGC-Argo chlorophyll-a profile, as $Z_{SCM}$, and recording BGC-Argo latitude and longitude data; step 4, model construction, including: matching the BGC-Argo latitude and longitude data with MODIS remote sensing reflectance (i.e., the target remote sensing reflectance data) corresponding to latitudes and longitudes, obtaining a grid point through BGC-Argo latitude and longitude positioning, obtaining remote sensing reflectance data of two grid points around the grid point, calculating groups of R values according to the remote sensing reflectance data of the two grid points, averaging the obtained groups of R values to obtain a group of data, and matching the groups of global measured BGC-Argo chlorophyll-a concentration profile data with the group of data to obtain a group of depths of SCM, taking the group of data as an input feature and the group of depths of SCM as an output feature to thereby obtain a matching data set, and drawing a scatter plot for $Z_{SCM}$ and R value by using the matching data set to thereby obtain a nonlinear model; and step 5, $Z_{SCM}$ calculation, including: obtaining, according to the nonlinear model obtained in the step 4, a function expression of the nonlinear model, and performing regression processing based on the function expression of the nonlinear model and the group of depths of SCM to obtain the depth of the SCM of the oceanic water body.

In an embodiment, in the step 2, the R value is a ratio obtained by an operation of the remote sensing reflectance corresponding to the band 412 nm, the remote sensing reflectance corresponding to the band 678 nm, and the remote sensing reflectance corresponding to the band 555 nm.

In an embodiment, a formula for calculating the R value is expressed as follows:

$$R = \frac{(Rrs_{412} - Rrs_{678})}{Rrs_{555}},$$

where $Rrs_{412}$ represents the remote sensing reflectance corresponding to the band 412 nm, $Rrs_{678}$ represents the remote sensing reflectance corresponding to the band 678 nm, and $Rrs_{555}$ represents the remote sensing reflectance corresponding to the band 555 nm.

In an embodiment, the function expression of the nonlinear model is expressed as:

$Z_{SCM} = a_0 + a_1 X + a_2 X^2.$

In an embodiment, an unknown number X is replaced with the R value obtained based on the remote sensing reflectance corresponding to the band 412 nm, the remote sensing reflectance corresponding to the band 678 nm, and the remote sensing reflectance corresponding to the band 555 nm, and the function expression of the nonlinear model is finally expressed as:

$$Z_{SCM} = a_0 + a_1 \frac{(Rrs_{412} - Rrs_{678})}{Rrs_{555}} + a_2 \left(\frac{(Rrs_{412} - Rrs_{678})}{Rrs_{555}}\right)^2.$$

In an embodiment, the calculating a depth of an SCM of each group of the groups of global measured BGC-Argo chlorophyll-a concentration profile data according to the BGC-Argo chlorophyll-a profile, as $Z_{SCM}$, specifically includes:

fitting the BGC-Argo chlorophyll-a profile by using a Gaussian kernel function to obtain the depth of the SCM of each group of the groups of global measured BGC-Argo chlorophyll-a concentration profile data, as $Z_{SCM}$;

where a formula for the fitting the BGC-Argo chlorophyll-a profile is expressed as:

$$Chla(z) = Chla_0 + \frac{h}{\sigma\sqrt{2\pi}} \exp\left[-\frac{(Z - Z_{scm})^2}{2\sigma^2}\right],$$

where $Chla_0$ represents a chlorophyll-a concentration at a sea surface, $\sigma$ represents a variance of subsurface chlorophyll-a concentration, h represents a total amount of the subsurface chlorophyll-a concentration within a Gaussian peak width (i.e., $4\sigma$), $Z_{SCM}$ represents a depth of a maximum concentration in the BGC-Argo chlorophyll-a profile, and Z represents a water depth.

In an embodiment, $a_0$, $a_1$ and $a_2$ are coefficients obtained by matching the groups of global measured BGC-Argo chlorophyll-a concentration profile data with the group of data and performing nonlinear fitting.

In an embodiment, in the step 2, the R value corresponding to $Z_{SCM}$ obtained by BGC-Argo is obtained by searching and matching a global R value corresponding latitudes, longitudes and time based on latitude and longitude data where the BGC-Argo is located.

In an embodiment, the method further includes: applying the depth of the SCM of the oceanic water body in determining a primary productivity of the oceanic water body, performing water ecological protection of the oceanic water body based on the primary productivity of the oceanic water body, and performing estimation of global carbon cycle and global climate change based on the primary productivity of the oceanic water body to perform environmental protection according to a estimation result to thereby achievie stability and sustainability of a global ecosystem.

(3) Beneficial Effects

Compared with the related art, the disclosure provides a method for inversing a depth of an SCM of an oceanic water body based on remote sensing reflectance, which has the following beneficial effects.

1. According to the disclosure, a nonlinear regression model is combined with remote sensing reflectance characteristics correpondings to three bands of 412 nm, 555 nm and 678 nm caused by vertical distribution of different chlorophyll-a concentrations to inverse a depth of an SCM of an ocean water body. This method can effectively contain optical characteristic signals caused by the vertical distribution of different chlorophyll-a concentrations, and can simply and quickly retrieve the depth of the SCM of the ocean water body by relying on the remote sensing reflectance data obtained by satellite remote sensing, with a small amount of calculation, which reduces the dependence of machine learning on chlorophyll-a concentrations, sea surface temperature data and sea surface height data, and reduces the calculation resource consumption of running machine learning.

2. Compared with the method for inversing the depth of the SCM based on the Gaussian kernel function model, the method for inversing a depth of an SCM of an oceanic water body based on remote sensing reflectance in the disclosure uses more optical characteristic signals, thus effectively improving the inversion accuracy.

3. By comparing a scatter plot of the depth of the SCM obtained by the method for inversing a depth of an SCM of an oceanic water body based on remote sensing reflectance in the disclosure with a scatter plot of the depth of the SCM obtained by global BGC-Argo data, it can be found that the method in the disclosure has a good effect on inversion of the depth of the SCM, with a mean absolute error (MAE) of 10.87, a determination coefficient R2 of 0.85 and a root mean square error (RMSE) of 13.75. The scatter distribution is concentrated near a function y=x, with a higher inversion accuracy, and a calculation time is only within 10 seconds on an ordinary desktop computer platform. The calculation amount is significantly reduced compared with the method for inversing the depth of the SCM based on the machine learning, effectively reducing the calculation resource consumption and inversion difficulty of inversing the SCM.

DETAILED DESCRIPTION OF EMBODIMENTS

In the following, the technical solutions in the embodiments of the disclosure will be clearly and completely described with reference to the attached drawings. Apparently, the described embodiments are only part of the embodiments of the disclosure, but not the whole embodiments. Based on the described embodiments in the disclosure, all other embodiments obtained by ordinary technicians in the field without creative labor belong to the scope of protection of the disclosure.

Embodiment 1

Figure 1:
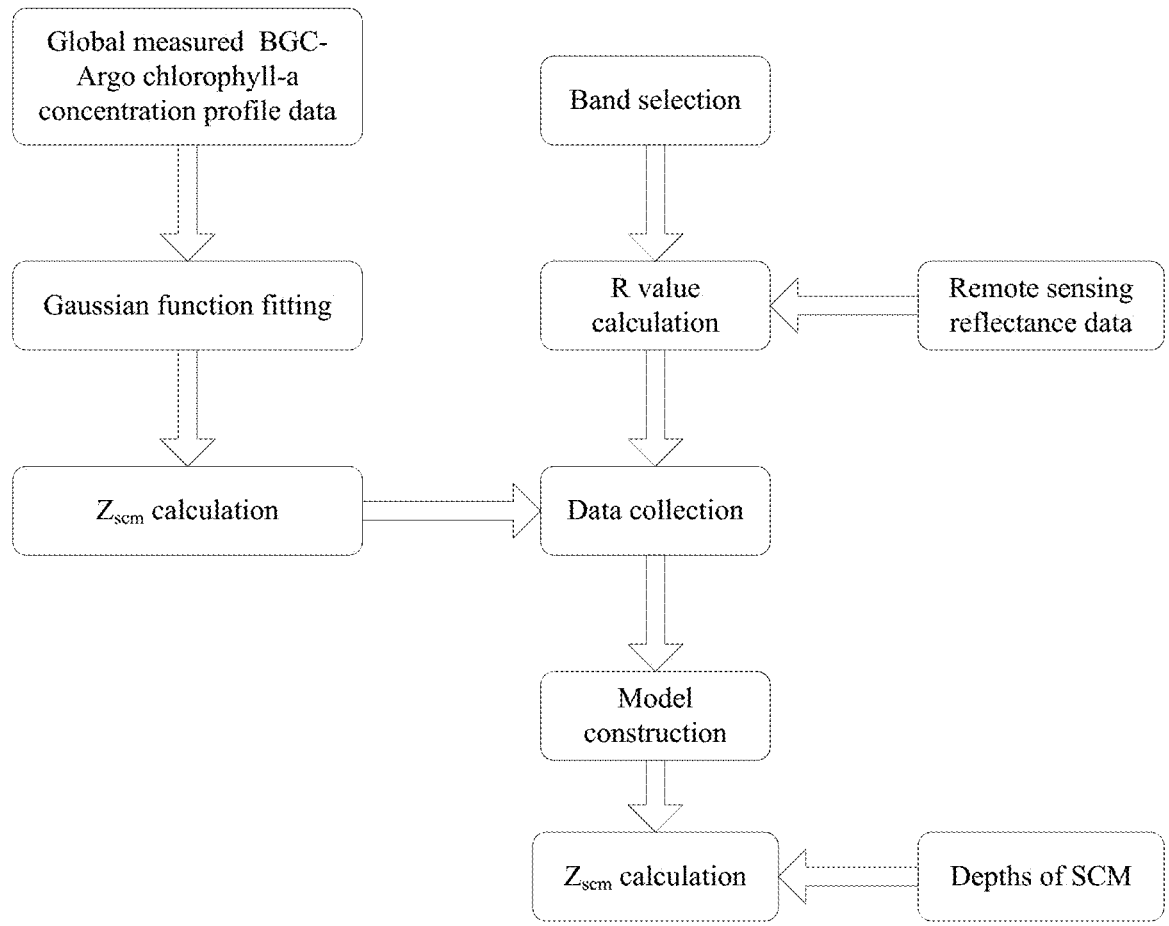
FIG. 1 illustrates a schematic flow chart of a method for inversing a depth of a subsurface chlorophyll-a maxima of an oceanic water body based on remote sensing reflectance according to an embodiment of the disclosure.
Figure 2:
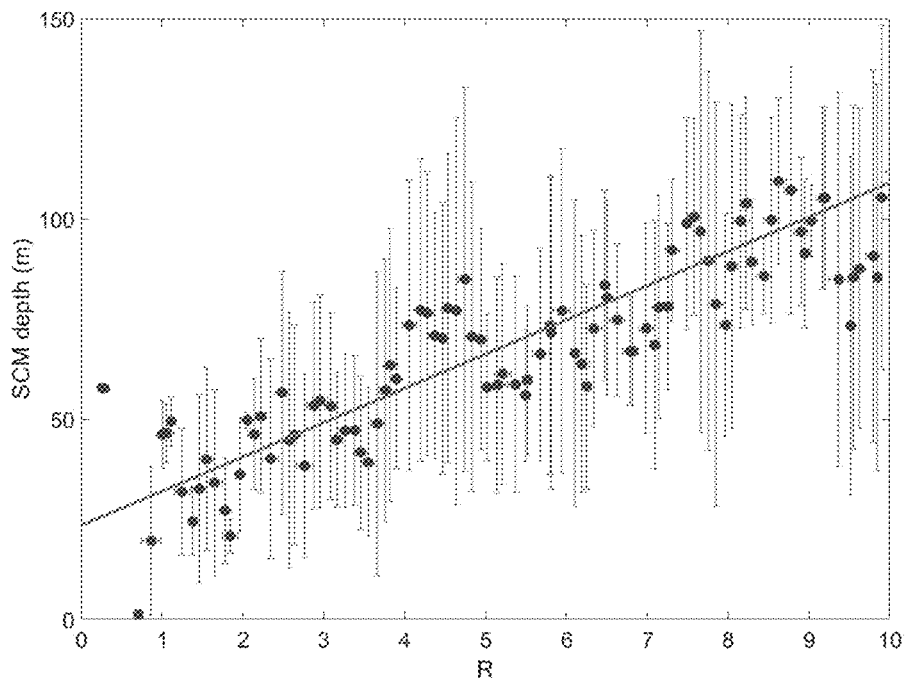
FIG. 2 illustrates a graph showing a depth regression relationship between R values and depths of the SCM (i.e., SCM depths) according to an embodiment of the disclosure.
Figure 3:
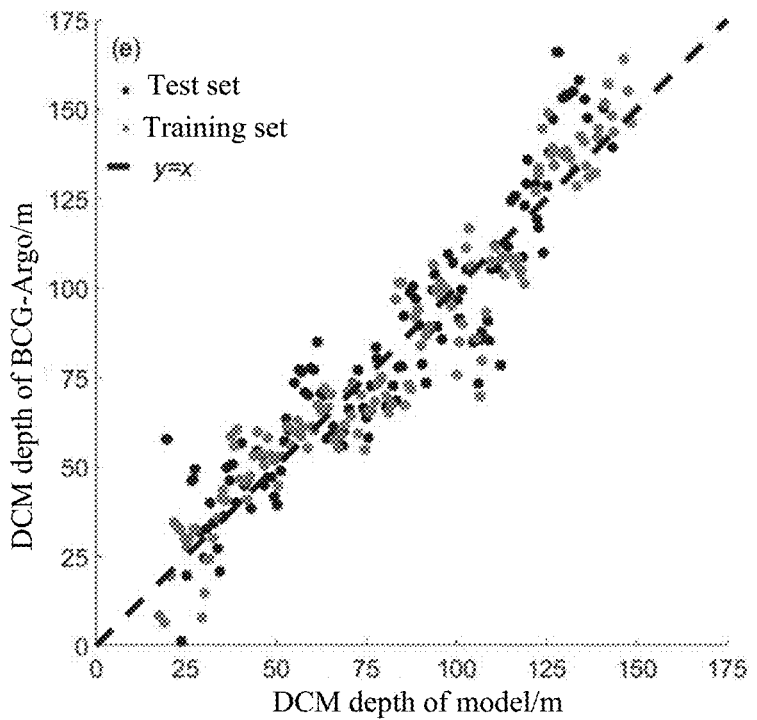
FIG. 3 illustrates a comparison diagram of the depth of the SCM inversed by the method of the disclosure and the depth of the SCM observed by the BGC-Argo.

Referring to FIGS. 1-3, a method for inversing a depth of a subsurface chlorophyll-a maxima of an oceanic water body based on remote sensing reflectance includes the following steps.

In step 1, band selection is performed, which specifically includes: obtaining a remote sensing reflectance data from a moderate-resolution imaging spectroradiometer (MODIS) remote sensing data, and selecting target remote sensing reflectance data corresponding to three bands of 412 nanometers (nm), 555 nm and 678 nm from the remote sensing reflectance data.

In step 2, R value calculation is performed, which specifically includes: calculating a difference between a remote sensing reflectance corresponding to the band 412 nm from the target remote sensing reflectance data and a remote sensing reflectance corresponding to the band 678 nm from the target remote sensing reflectance data, and calculating a ratio of the difference to a remote sensing reflectance corresponding to the band 555 nm from the target remote sensing reflectance data as a R value.

In step 3, data collection is performed, which specifically includes: obtaining groups of global measured biogeochemical-automatic reporting oceanographic observers (BGC-Argo) chlorophyll-a concentration profile data, fitting a BGC-Argo chlorophyll-a profile by using a Gaussian function according to the groups of global measured BGC-Argo chlorophyll-a concentration profile data, calculating a depth of an SCM of each group of the groups of global measured BGC-Argo chlorophyll-a concentration profile data according to the BGC-Argo chlorophyll-a profile, as $Z_{SCM}$, and recording BGC-Argo latitude and longitude data. The obtained groups of global measured biogeochemical-automatic reporting oceanographic observers (BGC-Argo) chlorophyll-a concentration profile data are data from an equatorial pacific, a northwest pacific, a southern ocean, an indian ocean, an atlantic ocean and other regions, which not only contain higher chlorophyll-a concentration regions, but also contain lower chlorophyll-a concentration regions, and have strong universality.

In step 4, model construction is performed, which specifically includes: matching the BGC-Argo latitude and longitude data with MODIS remote sensing reflectance corresponding to latitudes and longitudes, obtaining a grid point through BGC-Argo latitude and longitude positioning, obtaining remote sensing reflectance data of two grid points around the grid point, calculating groups of R values according to the remote sensing reflectance data of the two grid points, averaging the obtained groups of R values to obtain a group of data, and matching the groups of global measured BGC-Argo chlorophyll-a concentration profile data with the group of data to obtain a group of depths of SCM, taking the group of data as an input feature and the group of depths of SCM as an output feature to thereby obtain a matching data set, and drawing a scatter plot for $Z_{SCM}$ and R value by using the matching data set to thereby obtain a nonlinear model.

In step 5, $Z_{SCM}$ calculation is performed, which specifically includes: obtaining, according to the nonlinear model obtained in the step 4, a function expression of the nonlinear model, and performing regression processing based on the function expression of the nonlinear model and the group of depths of SCM to obtain the depth of the SCM of the oceanic water body. According to the disclosure, a nonlinear regression model is combined with remote sensing reflectance characteristics correpondings to three bands of 412 nm, 555 nm and 678 nm caused by vertical distribution of different chlorophyll-a concentrations to inverse a depth of an SCM of an ocean water body. This method can effectively contain optical characteristic signals caused by the vertical distribution of different chlorophyll-a concentrations, and can simply and quickly retrieve the depth of the SCM of the ocean water body by relying on the remote sensing reflectance data obtained by satellite remote sensing, with a small amount of calculation, which reduces the dependence of machine learning on chlorophyll-a concentrations, sea surface temperature data and sea surface height data, and reduces the calculation resource consumption of running machine learning.

In an embodiment of the disclosure, the R value is a ratio obtained by an operation of the remote sensing reflectance corresponding to the band 412 nm, the remote sensing reflectance corresponding to the band 678 nm, and the remote sensing reflectance corresponding to the band 555 nm.

In an embodiment of the disclosure, a formula for calculating the R value is expressed as follows:

$$R = \frac{(Rrs_{412} - Rrs_{678})}{Rrs_{555}},$$

where $Rrs_{412}$ represents the remote sensing reflectance corresponding to the band 412 nm, $Rrs_{678}$ represents the remote sensing reflectance corresponding to the band 678 nm, and $Rrs_{555}$ represents the remote sensing reflectance corresponding to the band 555 nm.

In an embodiment of the disclosure, the function expression of the nonlinear model is expressed as: $Z_{SCM} = a_0 + a_1 X + a_2 X^2$.

In an embodiment of the disclosure, an unknown number X is replaced with the R value obtained based on the remote sensing reflectance corresponding to the band 412 nm, the remote sensing reflectance corresponding to the band 678 nm, and the remote sensing reflectance corresponding to the band 555 nm, and the function expression of the nonlinear model is finally expressed as:

$$Z_{SCM} = a_0 + a_1 \frac{(Rrs_{412} - Rrs_{678})}{Rrs_{555}} + a_2 \left( \frac{(Rrs_{412} - Rrs_{678})}{Rrs_{555}} \right)^2.$$

In an embodiment of the disclosure, the calculating a depth of an SCM of each group of the groups of global measured BGC-Argo chlorophyll-a concentration profile data according to the BGC-Argo chlorophyll-a profile, as $Z_{SCM}$, specifically includes:

fitting the BGC-Argo chlorophyll-a profile by using a Gaussian kernel function to obtain the depth of the SCM of each group of the groups of global measured BGC-Argo chlorophyll-a concentration profile data, as $Z_{SCM}$;

where a formula for the fitting the BGC-Argo chlorophyll-a profile is expressed as:

$$Chla(z) = Chla_0 + \frac{h}{\sigma\sqrt{2\pi}} \exp\left[ -\frac{(Z - Z_{scm})^2}{2\sigma^2} \right],$$

where $Chla_0$ represents a chlorophyll-a concentration at a sea surface, $\sigma$ represents a variance of subsurface chlorophyll-a concentration, h represents a total amount of the subsurface chlorophyll-a concentration within a Gaussian peak width (i.e., $4\sigma$), $Z_{SCM}$ represents a depth of a maximum concentration in the BGC-Argo chlorophyll-a profile, and Z represents a water depth.

In an embodiment of the disclosure, $a_0$, $a_1$ and $a_2$ are coefficients obtained by matching the groups of global measured BGC-Argo chlorophyll-a concentration profile data with the group of data and performing nonlinear fitting.

In an embodiment of the disclosure, in the step 2, the R value corresponding to $Z_{SCM}$ obtained by BGC-Argo is obtained by searching and matching a global R value corresponding latitudes, longitudes and time based on latitude and longitude data where the BGC-Argo is located.

In an embodiment, the method further includes: applying the depth of the SCM to estimate a vertical distribution of the chlorophyll-a concentration, estimate a global carbon flux and a global primary productivity, and measure an ecological effect caused by global climate change.

By comparing a scatter plot of the depth of the SCM obtained by the method for inversing a depth of an SCM of an oceanic water body based on remote sensing reflectance in the disclosure with a scatter plot of the depth of the SCM obtained by global BGC-Argo data, it can be found that the method in the disclosure has a good effect on inversion of the depth of the SCM, with a mean absolute error (MAE) of 10.87, a determination coefficient R2 of 0.85 and a root mean square error (RMSE) of 13.75. The scatter distribution is concentrated near a function y=x, with a higher inversion accuracy, and a calculation time is only within 10 seconds on an ordinary desktop computer platform. The calculation amount is significantly reduced compared with the method for inversing the depth of the SCM based on the machine learning, effectively reducing the calculation resource consumption and inversion difficulty of inversing the SCM.

Embodiment 2

Referring to FIGS. 1-3, a method for inversing a depth of a subsurface chlorophyll-a maxima of an oceanic water body based on remote sensing reflectance includes the following steps.

In step 1, band selection is performed, which specifically includes: obtaining a remote sensing reflectance data from a moderate-resolution imaging spectroradiometer (MODIS) remote sensing data, selecting target remote sensing reflectance data corresponding to three bands of 412 nanometers (nm), 555 nm and 678 nm from the remote sensing reflectance data, and preprocessing the target remote sensing reflectance data to obtain target remote sensing reflectance data.

In step 2, R value calculation is performed, which specifically includes: calculating a difference between a remote sensing reflectance corresponding to the band 412 nm from the target remote sensing reflectance data and a remote sensing reflectance corresponding to the band 678 nm from the target remote sensing reflectance data, and calculating a ratio of the difference to a remote sensing reflectance corresponding to the band 555 nm from the target remote sensing reflectance data as a R value.

In step 3, data collection is performed, which specifically includes: obtaining groups of global measured biogeochemical-automatic reporting oceanographic observers (BGC-Argo) chlorophyll-a concentration profile data, fitting a BGC-Argo chlorophyll-a profile by using a Gaussian function according to the groups of global measured BGC-Argo chlorophyll-a concentration profile data, calculating a depth of an SCM of each group of the groups of global measured BGC-Argo chlorophyll-a concentration profile data according to the BGC-Argo chlorophyll-a profile, as $Z_{SCM}$, and recording BGC-Argo latitude and longitude data. The obtained groups of global measured biogeochemical-automatic reporting oceanographic observers (BGC-Argo) chlorophyll-a concentration profile data are data from an equatorial pacific, a northwest pacific, a southern ocean, an indian ocean, an atlantic ocean and other regions, which not only contain higher chlorophyll-a concentration regions, but also contain lower chlorophyll-a concentration regions, and have strong universality.

In step 4, model construction is performed, which specifically includes: matching the BGC-Argo latitude and longitude data with MODIS remote sensing reflectance corresponding to latitudes and longitudes, obtaining a grid point through BGC-Argo latitude and longitude positioning, obtaining remote sensing reflectance data of two grid points around the grid point, calculating R values according to the remote sensing reflectance data of the two grid points, averaging the obtained R values to obtain a group of data, and matching the groups of global measured BGC-Argo chlorophyll-a concentration profile data with the group of data to obtain a group of depths of SCM, taking the group of data as an input feature and the group of depths of SCM as an output feature to thereby obtain a matching data set, and drawing a scatter plot for $Z_{SCM}$ and R value by using the matching data set to thereby obtain a nonlinear model.

In step 5, $Z_{SCM}$ calculation is performed, which specifically includes: obtaining, according to the nonlinear model obtained in the step 4, a function expression of the nonlinear model, and performing regression processing based on the function expression of the nonlinear model and R values of remote sensing reflectance with different vertical distribution of chlorophyll-a concentration to obtain the depth of the SCM of the oceanic water body. According to the disclosure, a nonlinear regression model is combined with remote sensing reflectance characteristics correpondings to three bands of 412 nm, 555 nm and 678 nm caused by vertical distribution of different chlorophyll-a concentrations to inverse a depth of an SCM of an ocean water body. This method can effectively contain optical characteristic signals caused by the vertical distribution of different chlorophyll-a concentrations, and can simply and quickly retrieve the depth of the SCM of the ocean water body by relying on the remote sensing reflectance data obtained by satellite remote sensing, with a small amount of calculation, which reduces the dependence of machine learning on chlorophyll-a concentrations, sea surface temperature data and sea surface height data, and reduces the calculation resource consumption of running machine learning.

In an embodiment of the disclosure, the R value is a ratio obtained by an operation of the remote sensing reflectance corresponding to the band 412 nm, the remote sensing reflectance corresponding to the band 678 nm, and the remote sensing reflectance corresponding to the band 555 nm.

In an embodiment of the disclosure, a formula for calculating the R value is expressed as follows:

$$R = \frac{(Rrs_{412} - Rrs_{678})}{Rrs_{555}},$$

where $Rrs_{412}$ represents the remote sensing reflectance corresponding to the band 412 nm, $Rrs_{678}$ represents the remote sensing reflectance corresponding to the band 678 nm, and $Rrs_{555}$ represents the remote sensing reflectance corresponding to the band 555 nm.

In an embodiment of the disclosure, the function expression of the nonlinear model is expressed as: $Z_{SCM} = a_0 + a_1 X + a_2 X^2$.

In an embodiment of the disclosure, an unknown number X is replaced with the R value obtained based on the remote sensing reflectance corresponding to the band 412 nm, the remote sensing reflectance corresponding to the band 678 nm, and the remote sensing reflectance corresponding to the band 555 nm, and the function expression of the nonlinear model is finally expressed as:

$$Z_{SCM} = a_0 + a_1 \frac{(Rrs_{412} - Rrs_{678})}{Rrs_{555}} + a_2 \left( \frac{(Rrs_{412} - Rrs_{678})}{Rrs_{555}} \right)^2.$$

In an embodiment of the disclosure, the calculating a depth of an SCM of each group of the groups of global measured BGC-Argo chlorophyll-a concentration profile data according to the BGC-Argo chlorophyll-a profile, as $Z_{SCM}$, specifically includes:

fitting the BGC-Argo chlorophyll-a profile by using a Gaussian kernel function to obtain the depth of the SCM of each group of the groups of global measured BGC-Argo chlorophyll-a concentration profile data, as $Z_{SCM}$;

where a formula for the fitting the BGC-Argo chlorophyll-a profile is expressed as:

$$Chla(z) = Chla_0 + \frac{h}{\sigma\sqrt{2\pi}} \exp\left[-\frac{(Z - Z_{scm})^2}{2\sigma^2}\right],$$

where $Chla_0$ represents a chlorophyll-a concentration at a sea surface, $\sigma$ represents a variance of chlorophyll-a concentration, h represents a total amount of chlorophyll-a concentration within a Gaussian peak width (i.e., $4\sigma$), $Z_{SCM}$ represents a depth of a maximum concentration in the BGC-Argo chlorophyll-a profile, and Z represents a water depth.

In an embodiment of the disclosure, $a_0$, $a_1$ and $a_2$ are coefficients obtained by matching the groups of global measured BGC-Argo chlorophyll-a concentration profile data with the group of data and performing nonlinear fitting.

In an embodiment of the disclosure, R value data corresponding to $Z_{SCM}$ obtained by BGC-Argo is obtained by searching the global corresponding latitude and longitude and matching the R value corresponding to time through latitude and longitude data where BGC-Argo is located.

By comparing a scatter plot of the depth of the SCM obtained by the method for inversing a depth of an SCM of an oceanic water body based on remote sensing reflectance in the disclosure with a scatter plot of the depth of the SCM obtained by global BGC-Argo data, it can be found that the method in the disclosure has a good effect on inversion of the depth of the SCM, with a mean absolute error (MAE) of 10.87, a determination coefficient R2 of 0.85 and a root mean square error (RMSE) of 13.75. The scatter distribution is concentrated near a function y=x, with a higher inversion accuracy, and a calculation time is only within 10 seconds on an ordinary desktop computer platform. The calculation amount is significantly reduced compared with the method for inversing the depth of the SCM based on the machine learning, effectively reducing the calculation resource consumption and inversion difficulty of inversing the SCM.

It should be noted in the description of the disclosure that relational terms such as first and second are merely used to distinguish one entity or operation from another, and do not necessarily require or imply any actual relationship or order between these entities or operations. Moreover, the terms "include", "contain" or any other variants are intended to cover non-exclusive inclusion, so that the process, method, article or device that includes a series of elements not only includes those elements, but also includes other elements not explicitly listed, or also includes elements inherent to such a process, method, article, or device.

What is claimed is:

1. A method for inversing a depth of a subsurface chlorophyll-a maxima (SCM) of an oceanic water body based on remote sensing reflectance, the method comprising:

step 1, band selection, comprising: obtaining a remote sensing reflectance data from a moderate-resolution imaging spectroradiometer (MODIS) remote sensing data, and selecting target remote sensing reflectance data corresponding to three bands of 412 nanometers (nm), 555 nm and 678 nm from the remote sensing reflectance data;

step 2, R value calculation, comprising: calculating a difference between a remote sensing reflectance corresponding to the band 412 nm from the target remote sensing reflectance data and a remote sensing reflectance corresponding to the band 678 nm from the target remote sensing reflectance data, and calculating a ratio of the difference to a remote sensing reflectance corresponding to the band 555 nm from the target remote sensing reflectance data as a R value;

step 3, data collection, comprising: obtaining groups of global measured biogeochemical-automatic reporting oceanographic observers (BGC-Argo) chlorophyll-a concentration profile data, fitting a BGC-Argo chlorophyll-a profile by using a Gaussian function according to the groups of global measured BGC-Argo chlorophyll-a concentration profile data, calculating a depth of an SCM of each group of the groups of global measured BGC-Argo chlorophyll-a concentration profile data according to the BGC-Argo chlorophyll-a profile, as $Z_{SCM}$, and recording BGC-Argo latitude and longitude data;

step 4, model construction, comprising: matching the BGC-Argo latitude and longitude data with MODIS remote sensing reflectance corresponding to latitudes and longitudes, obtaining a grid point through BGC-Argo latitude and longitude positioning, obtaining remote sensing reflectance data of two grid points around the grid point, calculating groups of R values according to the remote sensing reflectance data of the two grid points, averaging the obtained the groups of R values to obtain a group of data, and matching the groups of global measured BGC-Argo chlorophyll-a concentration profile data with the group of data to obtain a group of depths of SCM, taking the group of data as an input feature and the group of depths of SCM as an output feature to thereby obtain a matching data set, and drawing a scatter plot for $Z_{SCM}$ and R value by using the matching data set to thereby obtain a nonlinear model; and step 5, $Z_{SCM}$ calculation, comprising: obtaining, according to the nonlinear model obtained in the step 4, a function expression of the nonlinear model, and performing regression processing based on the function expression of the nonlinear model and the group of depths of SCM to obtain the depth of the SCM of the oceanic water body.

2. The method for inversing the depth of the SCM of the oceanic water body based on remote sensing reflectance as claimed in claim 1, wherein in the step 2, the R value is a ratio obtained by an operation of the remote sensing reflectance corresponding to the band 412 nm, the remote sensing reflectance corresponding to the band 678 nm, and the remote sensing reflectance corresponding to the band 555 nm.

3. The method for inversing the depth of the SCM of the oceanic water body based on remote sensing reflectance as claimed in claim 2, wherein a formula for calculating the R value is expressed as follows:

$$R = \frac{(Rrs_{412} - Rrs_{678})}{Rrs_{555}},$$

where $Rrs_{412}$ represents the remote sensing reflectance corresponding to the band 412 nm, $Rrs_{678}$ represents the remote sensing reflectance corresponding to the band 678 nm, and $Rrs_{555}$ represents the remote sensing reflectance corresponding to the band 555 nm.

4. The method for inversing the depth of the SCM of the oceanic water body based on remote sensing reflectance as claimed in claim 1, wherein the function expression of the nonlinear model is expressed as: $Z_{SCM}=a_0+a_1X+a_2X^2$.

5. The method for inversing the depth of the SCM of the oceanic water body based on remote sensing reflectance as claimed in claim 4, wherein an unknown number X is replaced with the R value obtained based on the remote sensing reflectance corresponding to the band 412 nm, the remote sensing reflectance corresponding to the band 678 nm, and the remote sensing reflectance corresponding to the band 555 nm, and the function expression of the nonlinear model is finally expressed as:

$$Z_{SCM} = a_0 + a_1 \frac{(Rrs_{412} - Rrs_{678})}{Rrs_{555}} + a_2 \left( \frac{(Rrs_{412} - Rrs_{678})}{Rrs_{555}} \right)^2.$$

6. The method for inversing the depth of the SCM of the oceanic water body based on remote sensing reflectance as claimed in claim 5, wherein the calculating a depth of an SCM of each group of the groups of global measured BGC-Argo chlorophyll-a concentration profile data according to the BGC-Argo chlorophyll-a profile, as $Z_{SCM}$, specifically comprises:

fitting the BGC-Argo chlorophyll-a profile by using a Gaussian kernel function to obtain the depth of the SCM of each group of the groups of global measured BGC-Argo chlorophyll-a concentration profile data, as $Z_{SCM}$;

wherein a formula for the fitting the BGC-Argo chlorophyll-a profile is expressed as:

$$Chla(z) = Chla_0 + \frac{h}{\sigma\sqrt{2\pi}} \exp\left[-\frac{(Z-Z_{scm})^2}{2\sigma^2}\right],$$

where $Chla_0$ represents a chlorophyll-a concentration at a sea surface, $\sigma$ represents a variance of subsurface chlorophyll-a concentration, h represents a total amount of the subsurface chlorophyll-a concentration within a Gaussian peak width, $Z_{SCM}$ represents a depth of a maximum concentration in the BGC-Argo chlorophyll-a profile, and Z represents a water depth.

7. The method for inversing the depth of the SCM of the oceanic water body based on remote sensing reflectance as claimed in claim 6, wherein $a_0$, $a_1$ and $a_2$ are coefficients obtained by matching the groups of global measured BGC-Argo chlorophyll-a concentration profile data with the group of data and performing nonlinear fitting.

8. The method for inversing the depth of the SCM of the oceanic water body based on remote sensing reflectance as claimed in claim 7, wherein in the step 2, the R value corresponding to $Z_{SCM}$ obtained by BGC-Argo is obtained by searching and matching a global R value corresponding latitudes, longitudes and time based on latitude and longitude data where the BGC-Argo is located.

* * * * *